(12) United States Patent
Kordecki, Jr.

(10) Patent No.: US 9,536,448 B1
(45) Date of Patent: Jan. 3, 2017

(54) DEVICE AND METHOD FOR DISPLAYING PEDIATRIC MEDICAL INSTRUCTIONS

(71) Applicant: Stanley E. Kordecki, Jr., St. Petersburg, FL (US)

(72) Inventor: Stanley E. Kordecki, Jr., St. Petersburg, FL (US)

(73) Assignees: Stan Back Productions, Inc., St. Petersburg, FL (US); Medical Emergency Device Innovation Corporation, St. Petersburg, FL (US)

( * ) Notice: Subject to any disclaimer, the term of this patent is extended or adjusted under 35 U.S.C. 154(b) by 341 days.

(21) Appl. No.: 14/511,484

(22) Filed: Oct. 10, 2014

Related U.S. Application Data (60) Provisional application No. 61/889,673, filed on Oct. 11, 2013.

(51) Int. Cl.
*A61B 5/107* (2006.01)
*A61B 10/00* (2006.01)
*G09B 19/00* (2006.01)

(52) U.S. Cl.
CPC .............. *G09B 19/00* (2013.01); *A61B 5/107* (2013.01); *A61B 10/00* (2013.01)

(58) Field of Classification Search
CPC ............................... A61B 5/107; A61B 10/00
USPC ........................................... 33/512; 283/900
See application file for complete search history.

(56) References Cited

U.S. PATENT DOCUMENTS

| | | |
|---|---|---|
| 4,713,888 A | 12/1987 | Broselow |
| 4,823,469 A | 4/1989 | Broselow |
| 5,010,656 A | 4/1991 | Broselow |
| 5,984,368 A * | 11/1999 | Cain ................. A61B 90/90 283/115 |
| 6,132,416 A | 10/2000 | Broselow |
| 7,475,487 B1 * | 1/2009 | Johnson .............. A61B 5/1072 33/493 |
| 7,770,301 B1 * | 8/2010 | Grandberry ........... G01B 3/004 33/494 |
| 2006/0000480 A1 * | 1/2006 | Broselow ............... A61M 5/14 128/898 |
| 2006/0137696 A1 | 6/2006 | Broselow |
| 2008/0184576 A1 | 8/2008 | Hodgetts et al. |
| 2009/0126743 A1 | 5/2009 | Wingert |

(Continued)

*Primary Examiner* — Christopher Fulton
(74) *Attorney, Agent, or Firm* — Michele L. Lawson; Smith & Hopen, P.A.

(57) ABSTRACT

A device, method and system for displaying medical information/instructions is presented. The device is comprised generally of an elongated base displaying a plurality of color-coded zones having a plurality of removable instruction portions attached which correspond to each color zone. The instruction portion is generally comprised of fastener and a medical information/instruction display. The medical information/instruction display can be at least one sheet on which the medical information/instructions are printed or an electronic display such as an LCD screen. If printed information/instructions are used, each sheet may be contained within a transparent sleeve to protect the sheet from damage. In use, a child's weight is correlated to a specific color zone on the elongated base and the corresponding instruction portion is removed and fastened to an object near the child to easily enable the user to administer medical treatment to the child.

20 Claims, 8 Drawing Sheets

(56) References Cited

U.S. PATENT DOCUMENTS

2013/0023793 A1* 1/2013 Valencia .............. A61B 5/1072
 600/587
2013/0330695 A1* 12/2013 Antevy ................. G09B 23/28
 434/262

* cited by examiner

DEVICE AND METHOD FOR DISPLAYING PEDIATRIC MEDICAL INSTRUCTIONS

CROSS REFERENCE TO RELATED APPLICATIONS

This application is a nonprovisional of and claims priority to U.S. Provisional Patent Application 61/889,673, entitled "Device and Method for Displaying Pediatric Medical Instructions", filed Oct. 11, 2013, the contents of which are herein incorporated by reference.

FIELD OF INVENTION

This invention relates to devices used to display medical information/instructions. Specifically, the invention provides a novel device which can be positioned on or near the user or patient to show the precise medical information/instructions including dosages and medical equipment sizes necessary to treat a patient, particularly a pediatric patient in an emergency situation.

BACKGROUND OF THE INVENTION

Resuscitation tapes are routinely used to correlate a child's length/height and/or his/her weight to a specific color zone on the tape in order to provide medical instructions in an emergency situation. The resuscitation tape is divided into several color-coded zones which correspond to various heights and weight ranges. Each color-coded section applies to a specific weight range and provides medical dosages and equipment sizes that are suitable for a child in that weight range.

Once the child's color zone is determined, the specific instructions for that color zone can be utilized to provide medical instructions such as medication dosages, equipment sizes, ventilator settings, and shock voltage when using a defibrillator.

One problem with the resuscitation tapes currently available is that they are cumbersome for the medical professional to read the medical instructions. The medical professional must unfold the tape each time he/she needs to consult it for dosages and/or equipment sizing for the child. This can waste valuable time in an emergency situation. What is needed is a device in which the user can quickly and easily access medical information for a child in an emergency situation.

SUMMARY OF INVENTION

The present invention relates to a device which correlates to the color zones on a resuscitation tape and which makes it faster and easier to access the color zone information without folding and unfolding the tape, thus saving precious moments in an emergency situation.

The device is comprised generally of an elongated base divided into color-coded sections which are correlated to the color-coded sections on a resuscitation tape. A plurality of color-coded instruction portions which correspond to color-coded sections on the base are positioned along the length of the base. The elongated base may have retaining device to removably attach the plurality of color-coded instruction portions which correspond to the color-coded sections on the elongated base. Retaining device may include such systems as a hook and loop system, a button system, a snap system, a zipper system, a magnet system, a hook and eye system, a tie system, etc.

Alternatively, retaining device may be in the form of a plurality of separate containment devices including, but not limited to, pouches, sleeves, pockets, straps, clips, cradle structures, etc., each of which may contain one instructional portion.

Each instruction portion is comprised of a medical information/instruction display attached to fastener. The medical information/instruction display may take many forms including at least one sheet having printed medical information/instructions and an electronic display screen powered by a microprocessor integrated into the device which displays the medical information/instructions. If printed medical information/instructions are used, each sheet may be inserted into a transparent sleeve to protect the sheet from damage. Alternatively, each sheet may be coated with a substance to prevent damage.

The fastener is capable of removably attaching to an object such as the user's wrist/arm or clothing, the child's limb or clothing, a person's limb or clothing that is adjacent to the child, or an inanimate object that is adjacent to the child such as a bed railing. Any fastener that is capable of removably attaching instruction portion to an object is contemplated by the invention. In an embodiment, fastener is a tubular band that may be elasticized.

In use, the child's length/height or weight is first determined. The child may be measured using a resuscitation tape, such as the Broselow® tape or Pediatape, to determine which color zone the child falls into. Alternatively, the child may be weighed to determine which color zone the child falls into. Once the color zone of the child is determined, the medical professional/user may remove the instruction portion of the device corresponding to the determined color zone of the child from the elongated base. The instruction portion would then be removably attached to an object such as the arm/wrist of the user, the limb of the child or an inanimate object/surface or other person adjacent the child thus allowing medical information specifically tailored to the child to be readily accessible to the medical professional/user while caring for the child.

A system for displaying medical information/instructions is also contemplated by the inventors in which the device described above as being comprised of an elongated base divided into color-coded sections and having removably attachable instruction portions is used to make the medical information associated with the determined color zone of the child easily accessible through removably attaching the instruction portion of the corresponding color zone to an object.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

DEFINITIONS

As used in the specification and claims, the singular form "a", "an" and "the" include plural references unless the context clearly dictates otherwise.

The terms "medical professional" and "user" are used synonymously herein.

The terms "sheet", "paper", and "card" are used synonymously herein.

"Resuscitation tape" as used herein refers to a standardized color-coded tape measure that is used for pediatric emergencies. Examples of such a tape include the Broselow® tape and the Pediatape. Resuscitation tapes correlate the child's length/height and/or his/her weight to a specific color zone on the tape in order to provide medical instructions specific to a child of that size. The tape is divided into several color-coded zones which correspond to various height/length and weight ranges. Each color coded section applies to a specific weight range and provides medical dosages and equipment sizes that are suitable for that weight range. Table 1 below refers to the various color zones and corresponding weights/lengths.

"Color-coded zones" as used herein refers to color-coded sections on the device which correspond to the standardized color zones on a pediatric resuscitation tape. Each color zone corresponds to a specific range of weights/lengths of a child as shown in Table 1 below.

"Base" as used herein refers to an object onto which the instruction portions are attached when not in use. This object may be rigid or flexible according to the particular embodiment.

"Instruction portion" as used herein refers to the portion of the device which can be removably attached to an object and to the base so as to allow the user to view medical instructions/information that are contained therein.

"Medical information/instruction display" as used herein refers to the portion of the instruction portion of the device showing medical information/instructions. The medical instructions/information may be in physical or electronic forms, such as printed sheets or an electronic display. If in the form of printed sheets, the sheets may be encased within one or more transparent sleeves to protect the sheets from damage. Alternatively, the sheets may be coated with a substance which protects them from damage.

"Fastener" as used herein refers to the portion of the instruction portion of the device which physically attaches to an object, including a person as well as an inanimate object. The fastener may be in the form of at least one strap such as a tubular band, a strap having a hook and loop closure system; a strap having a buckle closure system, similar to a belt; a strap having a magnetic closure system; a strap having a snap closure system; a strap having a button closure system; a tie system; and a strap having a hook and eye closure system.

"Object" as used herein refers to a physical or tangible thing that is relatively stable in form. Specifically as used herein, object refers to a thing to which the information portion of the device may be attached. This includes body parts and clothing of a user or other person as well as body parts and clothing of the child. In addition, the definition includes any physical surface or inanimate thing such as bed railing which is near the child/patient as long as the user is capable of easily viewing the medical instruction/information.

"Adjacent" as used herein refers to being in close proximity or nearby. As used herein, an object that is adjacent to the child refers to an object that is close by the child so as to allow the user to be able to easily view the medical instructions.

"Retaining device" as used herein refers to any means capable of retaining instruction portion on elongated base. In some embodiments, retaining device may be continuous and extend longitudinally on base from first color zone to last color zone. Alternatively, separate retaining device may be used in each color zone to attach that specific instruction portion to the specific color zone. Examples of retaining device include, but are not limited to, hook and loop system, a button system, a snap system, a zipper system, a magnet system, a hook and eye system, a tie system, etc. In an alternative embodiment, retaining device may be in the form of a plurality of separate containment devices which contain instruction portions within base. Examples of such containment devices include, but are not limited to, pouches, sleeves, pockets, straps, clips, cradle structures, etc., each of which may contain one instruction portion.

Dosing of medications for pediatric patients can be a complicated endeavor and much time can be wasted while the medical professional looks up dosages for various medications. In order to alleviate this problem, resuscitation tapes were developed which feature a color-coded measuring and dosing system that is the standard among medical professionals. The first of these resuscitation tapes was the Broselow® tape or Broselow® pediatric tape, which is a color-coded tape measure that is used throughout the world for pediatric emergencies. The tape is recognized as the standard for emergency treatment for children. The method and device are covered under U.S. Pat. Nos. 4,713,888; 4,823,469; and 5,010,656 as well as U.S. Patent Application Publication No. US 2006/0137696, herein incorporated in their entirety by reference.

Resuscitation tapes such as the Broselow® tape correlate the child's length/height and/or his/her weight to a specific color zone on the tape in order to provide medical instructions. The tape is divided into several color-coded zones which correspond to various height/length and weight ranges. Each color coded section applies to a specific weight range and provides medical dosages and equipment sizes that are suitable for that weight range. In instances in which the child's weight is known then weight is used to determine the color zone. In instances where the child's weight is not known, height/length may be used to determine the child's color zone.

Once the child's color zone is determined, the specific instructions for that color zone can be utilized to provide medical instructions such as medication dosages, equipment sizes, ventilator settings, and shock voltage when using a defibrillator. The tape may be used for a child up to age 12 and approximately up to about 80 pounds. An example of the color-coded zones is shown in Table 1 below.

TABLE 1

| Color | Estimated Weight (in kilograms) | Estimated Weight (in pounds) |
| --- | --- | --- |
| Grey | 3-5 kgs | 6-11 lbs |
| Pink | 6-7 kgs | 13-15 lbs |
| Red | 8-9 kgs | 17-20 lbs |
| Purple | 10-11 kgs | 22-24 lbs |
| Yellow | 12-14 kgs | 26-30 lbs |
| White | 15-18 kgs | 33-40 lbs |
| Blue | 19-23 kgs | 42-50 lbs |
| Orange | 24-29 kgs | 53-64 lbs |
| Green | 30-36 kgs | 66-80 lbs |

As stated previously, one problem with the current resuscitation tapes is that it is cumbersome for the medical professional to unfold the tape each time he/she needs to consult it for dosages and/or equipment sizing for the child. This can waste valuable time in an emergency situation. The inventors have developed a device based on resuscitation tapes such as the Broselow® tape which makes it faster and easier to access the color zone information without folding and unfolding the tape, thus saving precious moments in an emergency situation.

Although the present invention will be described with reference to the embodiments shown in the drawings, it should be understood that the present invention can be embodied in many alternate forms of embodiments. In addition, any suitable size, shape, or type of elements or materials can be used.

Figure 1:
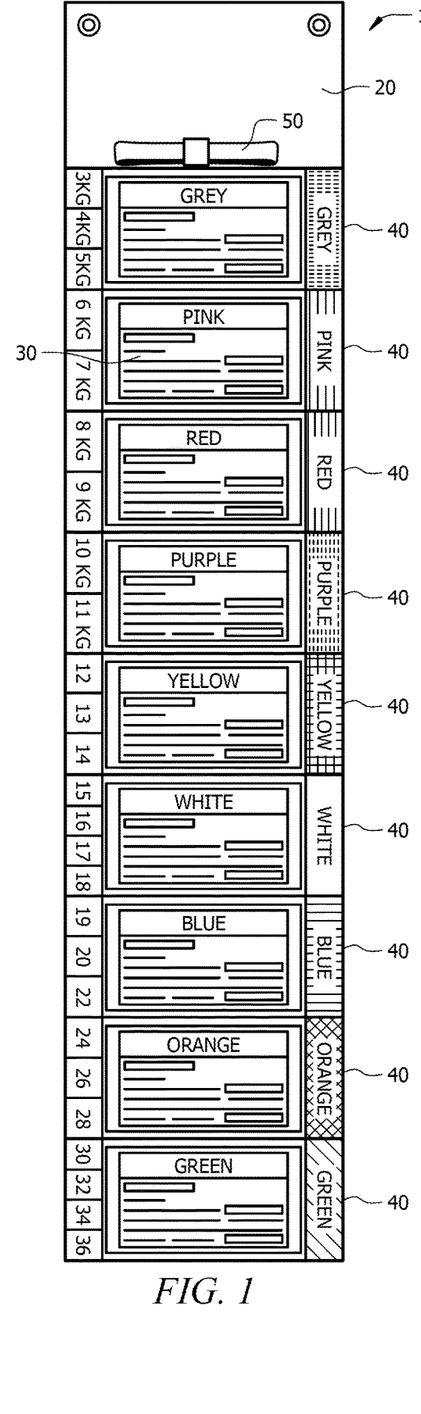
FIG. 1 is a front view of the device with the instruction portions attached to the device.
Figure 2:
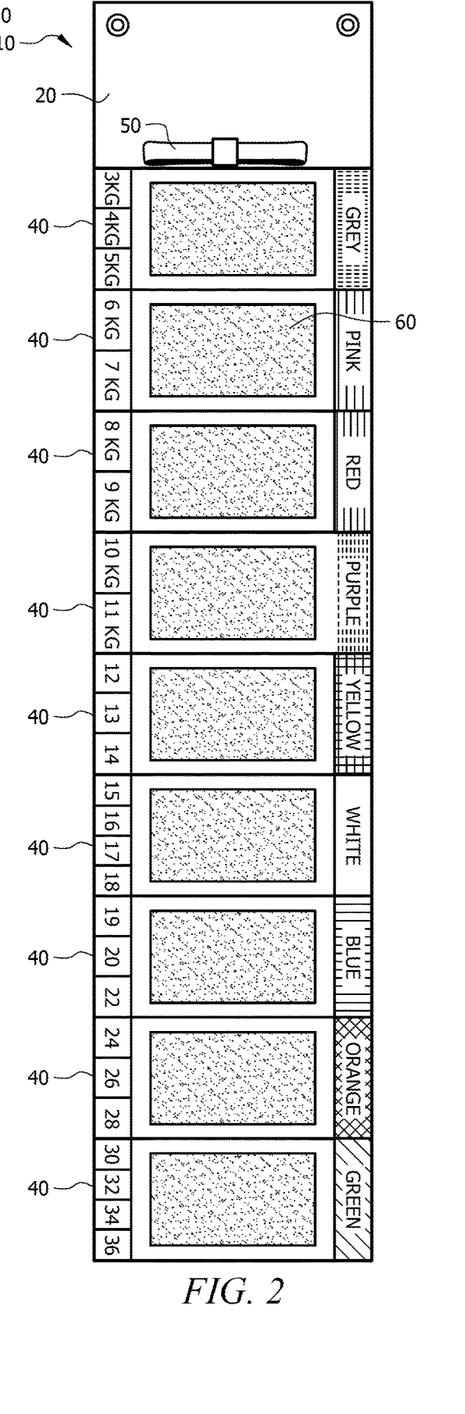
FIG. 2 is a front view of the device without the instruction portions attached.

As depicted in FIGS. 1 and 2, device 10 is comprised of elongated base 20 having a proximal end, a distal end, a front side and a back side. In an embodiment, the front side of elongated base 20 may depict color-coded sections/zones 40 dispersed longitudinally along base 20. Color-coded zones 40 correspond to the color zones depicted on standard resuscitation tapes such as the Broselow® tape.

In an embodiment, color zones 40 are arranged from the proximal end of base 20 to the distal end of base 20 in ascending weight number as depicted in Table 1. In this embodiment, the color grey is located at the proximal end of base 20 and the color green is located at the distal end of base 20. In an alternate embodiment, color zones 40 may be arranged from proximal end of base 20 to the distal end of base 20 in descending weight number. In this embodiment, the color green is located at the proximal end of base 20 and the color grey is located at the distal end of base 20. Regardless of whether color zones 40 are arranged in ascending or descending order, the order of the colors is always the same. For example, pink is always between grey and red, purple is always between red and yellow, etc. Keeping the order of the colors the same allows rapid identification of the color zone of the child since the colors will always be positioned according to ascending or descending weight of the child.

Color zones 40 may be depicted on elongated base 20 by physically coloring all or only a portion of each zone the corresponding color and/or having the corresponding color's name printed in each zone. Each color zone 40 may also contain the corresponding weights to that particular color zone. Alternatively to coloring all or a portion of base 20 itself, base 20 may be of a solid color and retaining device 60 may be colored in part or in whole.

Figure 3:
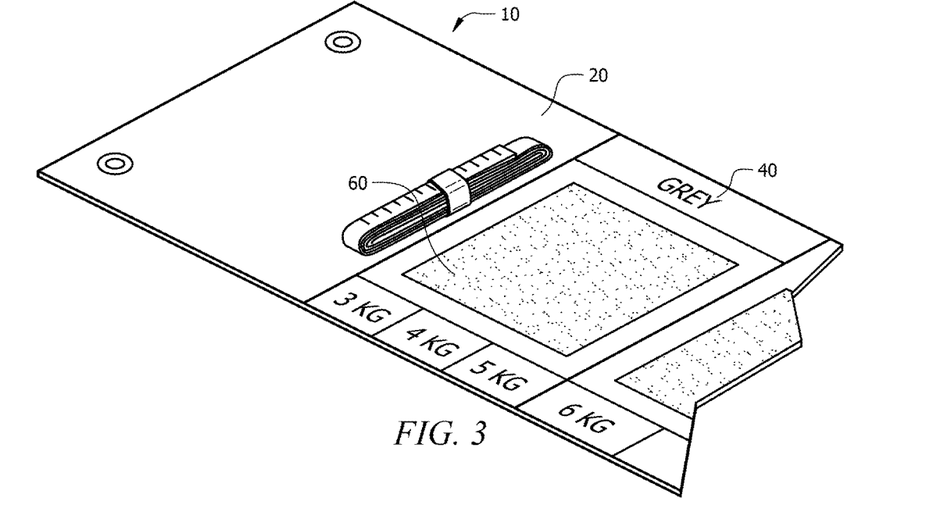
FIG. 3 is a perspective view of a portion of the device without the instruction portion attached and showing the storage of the measuring tape.
Figure 4:
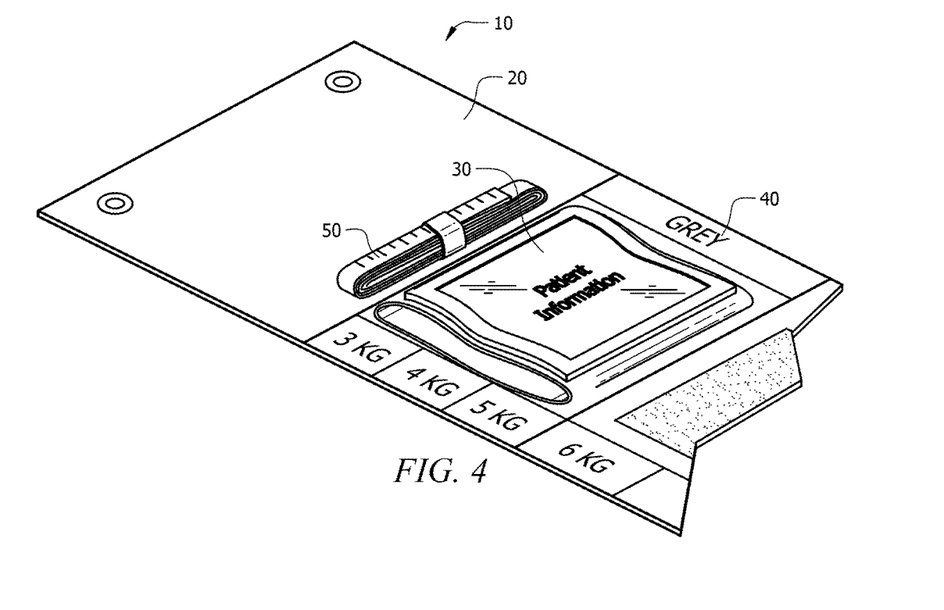
FIG. 4 is a perspective view of a portion of the device having the instruction portions attached.
Figure 5:
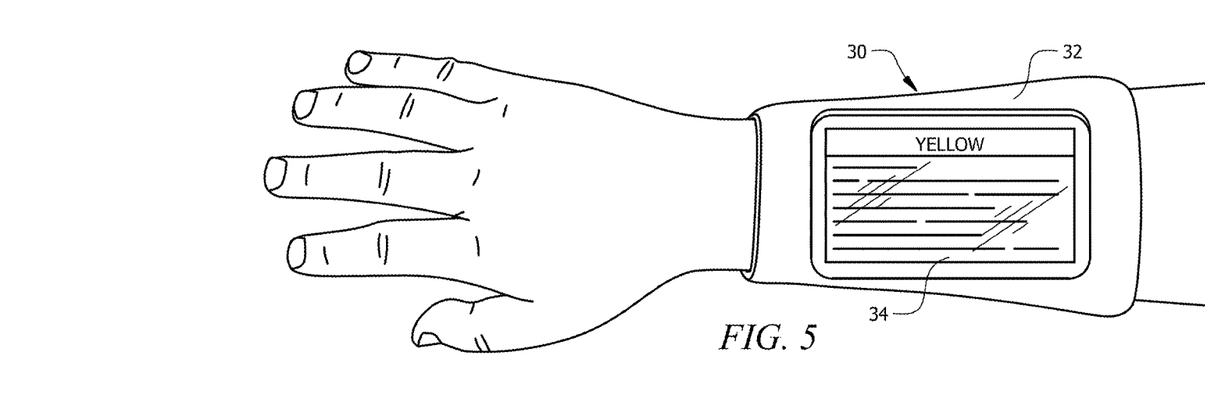
FIG. 5 is a front view of the instruction portion of the device.

In an embodiment, each color zone 40 may have a separate retaining device 60 as depicted in FIGS. 2 and 3. Alternatively, retaining device 60 may be continuous and extend longitudinally on base 20 from first color zone 40 to last color zone 40 allowing instruction portions 30 to attach to base 20 in the corresponding color zone 40 using only one retaining device 60. Retaining device 60 may include any means capable of attaching instruction portions 30 of device 10 as indicated in FIGS. 1 and 4. Examples of retaining device 60 that may be used in this embodiment include, but are not limited to, a hook and loop system, a button system, a snap system, a zipper system, a magnet system, a hook and eye system, a tie system, etc. In an alternative embodiment, illustrated in FIGS. 10 and 11 as described subsequently, retaining device 60 may be in the form of a plurality of separate containment devices 80 including, but not limited to, pouches, sleeves, pockets, straps, clips, cradle structures, etc., each of which may contain one instruction portion 30.

Elongated base 20 may be manufactured from a variety of materials capable of holding instruction portions 30 of device 10. In some embodiments, elongated base 20 may be manufactured of a hard material including, but not limited to, hardened plastic, wood, metal, etc. This embodiment is particularly beneficial for hanging/mounting device 10 on a wall or other surface, for example in an emergency room of a hospital. In this embodiment, the proximal end of elongated base 20 may have means to hang or mount the device on a wall or other support. Such hanging or mounting means are well known by those of ordinary skill in the art. In other embodiments, elongated base 20 is manufactured from a more flexible material including, but not limited to, fabric, thickened paper, vinyl, flexible plastic, nylon, etc. This embodiment is particularly beneficial for use in a more mobile situation such as in an ambulance as this embodiment allows elongated base 20 to be compacted into a smaller shape for storage. In this embodiment, device 10 may have a closure means such as a hook and loop system, a button system, a snap system, a zipper system, a magnet system, a hook and eye system, a tie system, etc. to fasten the ends of device 10 together to form a more compact shape.

As depicted in the Figures, the proximal end of elongated base 20 may contain retaining device, similar to those used for instruction portions 30, which may retain a resuscitation tape such as the Broselow® tape or the Pediatape on base 20. The retaining device may fully encase tape 50 or may only encase a portion of tape 50 as depicted in FIGS. 1-4. The retaining device for tape 50 includes, but is not limited to, pouches, sleeves, pockets, straps, clips, cradle structures, etc. The retaining device for tape 50 may be transparent so that the tape can be viewed through the retaining device.

Instruction portion 30 of device 10 may be comprised of medical information/instruction display 34 affixed to fastener 32. Medical information/instruction display 34 may be affixed to fastener 32 by any attachment means known to those of ordinary skill in the art including, but not limited to, removably affixable means such as a hook and loop system, a button system, a snap system, a zipper system, a magnet system, a tie system, and a hook and eye system, as well as more permanent affixing means such as gluing, sewing, etc.

Medical information/instruction display 34 may take any form which allows the user to easily and quickly visually access the child's medical information/instructions based on their determined color zone. Examples of medical information/instruction display 34 include, but are not limited to, at least one information/instruction sheet which contains printed medical information/instructions and an electronic display screen powered by a microprocessor integrated into the device which displays the medical information/instructions for each color zone. In an embodiment, the information/instruction sheet(s) may be inserted into at least one transparent sleeve 36 which allows the information/instructions to be viewed through sleeve 36 on at least one side of sleeve 36. Transparent sleeve 36 may be made of a durable plastic or other material as long as it is transparent so as to allow viewing of medical information/instruction sheet. Alternatively, medical information/instruction sheet itself may be coated with a substance such as a flexible plastic to protect it from damage.

The medical information/instructions for each color zone 40 include universal dosing units that are standard in the art. Each color zone 40 has a plurality of treatment values that are correlated to the child's weight. In the embodiments having printed medical information/instructions, the medical information/instructions may be printed on colored paper corresponding to each color zone, may be printed on at least one paper/card and have the corresponding color, or alternatively the name of the corresponding color, printed on the paper/card to identify the color zone to which each of the medical information/instructions corresponds to. Similarly in the electronic display embodiment, the display may show either lettering to represent the respective color zone or the screen for the each zone may display the respective color.

In an embodiment, fastener 32 of instruction portion 30 of device 10 may take the form of at least one strap having a front side and a back side and is capable of attaching to an object adjacent the child or to the child himself. Fastener 32 may take several forms including, but not limited to, a tubular band which may be elasticized to accommodate a wide variety of users; a strap having a hook and loop closure system; a strap having a buckle closure system, similar to a belt; a strap having a magnetic closure system; a strap having a snap closure system; a strap having a button closure system; a tie system; and a strap having a hook and eye closure system. Fastener 32 includes all embodiments capable of removably affixing instruction portion 30 to an object so that medical information/instruction display 34 may be easily viewed by the user. Instruction portion 30 of device 10 may be removably affixed to an object such as the user's arm/wrist or clothing, one of the child/patient's limbs or clothing, a person or their clothing that is adjacent to the child, a surface nearby the child/patient such as a bed railing, etc. One of ordinary skill in the art would recognize various embodiments that would encompass fastener 32 as well as various objects to which instruction portion 30 may removably attach. In some embodiments, all or a portion of fastener 32 may be colored to correspond to each color zone 40.

Medical information/instruction display 34 may be affixed to fastener 32. In embodiments using elongated base 20 in which retaining device 60 are not separate containment devices 80, such as the embodiments shown in FIGS. 2 and 3, fastener 32 may be at least one strap having a front side and a back side. As used herein the term "strap" includes a tubular band in varying widths/lengths. In this embodiment, the back side of fastener 32 may contain a portion of the system of retaining device 60 which corresponds to the portion of the system of retaining device 60 that are located on the front side of elongated base 20. For example, if a hook and loop system is used as retaining device 60, the back side of the at least one strap may have loop material positioned thereon while the front side of elongated base 20 may have the corresponding hook material positioned thereon to allow instruction portion 30 to removably attach to base 20. Retaining device that may be used in this embodiment include, but are not limited to, hook and loop system, a button system, a snap system, a zipper system, a magnet system, a tie system, and a hook and eye system. In each of these systems, one portion of the system is positioned on fastener 32 and the corresponding portion of the system is positioned on elongated base 20. One of ordinary skill in the art would recognize removable retention systems that may be used with the device.

FIGS. 5-9 depict an exemplary embodiment of instruction portion 30 of device 10 in which fastener 32 is in the form of a tubular band and medical information/instruction display 34 is in the form of printed medical information/instructions corresponding to the particular color zone positioned within at least one transparent sleeve 36. In this embodiment, instruction portion 30 is comprised of fastener 32, which is a tubular band having a front side, a back side, and first and second opposed ends as well as medical information/instruction display 34. The opposing ends of tubular band are adapted to receive therethrough the hand and wrist of a user or other person or a limb of the child. The tubular band may also be used to attach instruction portion 30 to a surface near the child such as a bed railing. The tubular band may be elasticized in some embodiments. In some embodiments, the tubular band may be colored to correspond to the individual color zone 40 on elongated base 20 onto which it is removably attached. Medical information/instruction display 34 may be in the form of printed information/instructions inserted in to at least one transparent sleeve 36 having a front surface, a back surface, a top edge, a bottom edge and opposing ends. In the embodiment shown in FIG. 5, medical information/instruction display 34 contained within at least one transparent sleeve is affixed to the front side of the tubular band.

Figure 6:
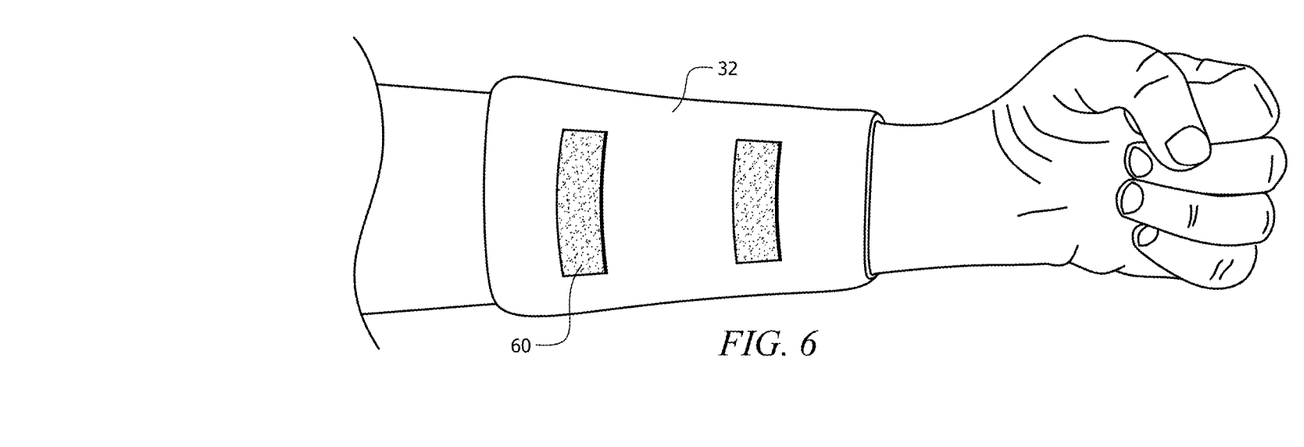
FIG. 6 is a back view of the instruction portion of the device.

As illustrated in FIG. 6 and described previously, in some embodiments, the back side of the tubular band may contain a portion of the system of retaining device 60 for removably attaching instruction portion 30 of device 10 to elongated base 20.

Figure 7:
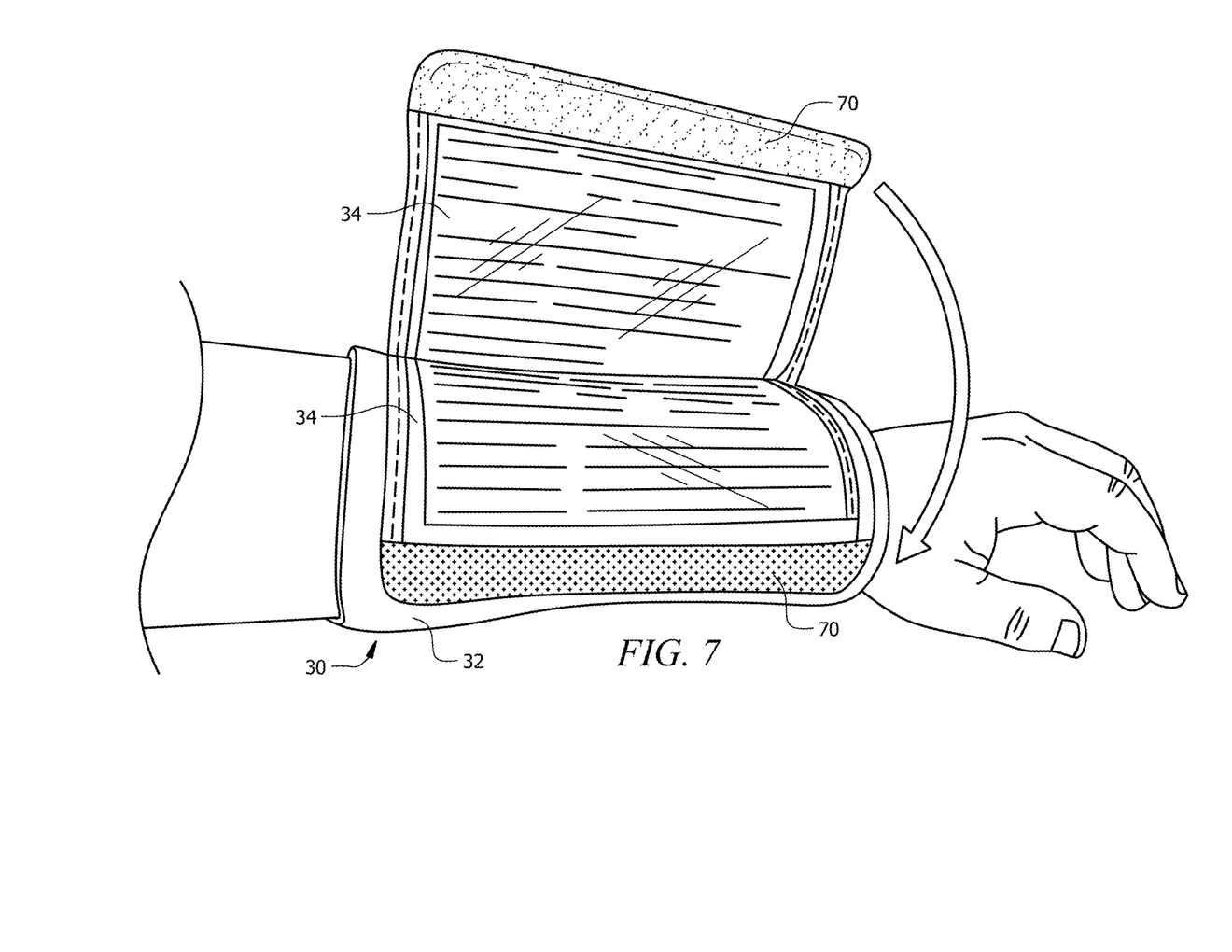
FIG. 7 is a front view of the instruction portion of the device showing one of the transparent sleeves in a raised position.
Figure 8:
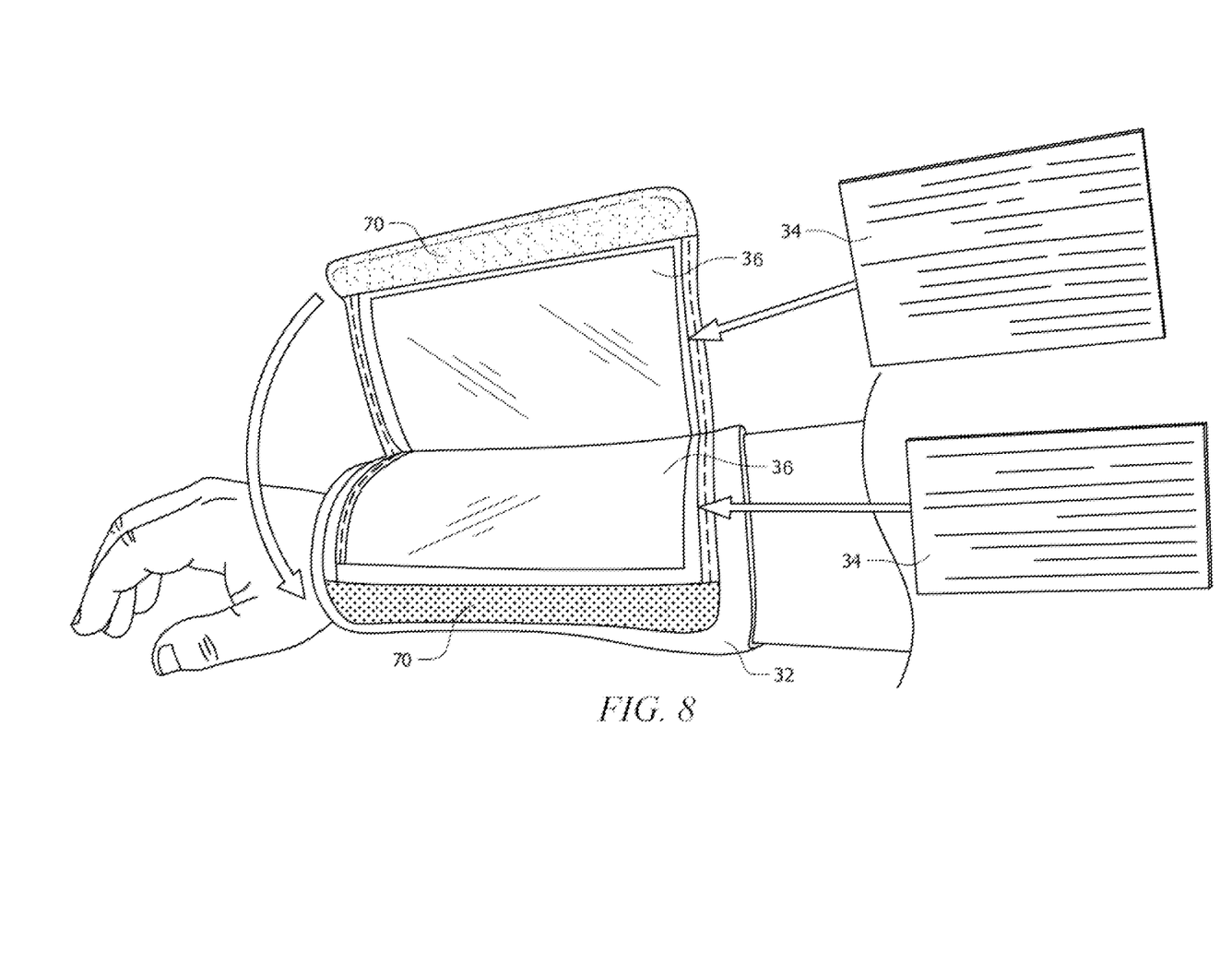
FIG. 8 is a front view of the instruction portion of the device showing one of the transparent sleeves in a raised position and illustrating that patient information/medical instructions may be placed into the various sleeves of the instruction portion of the device.
Figure 9:
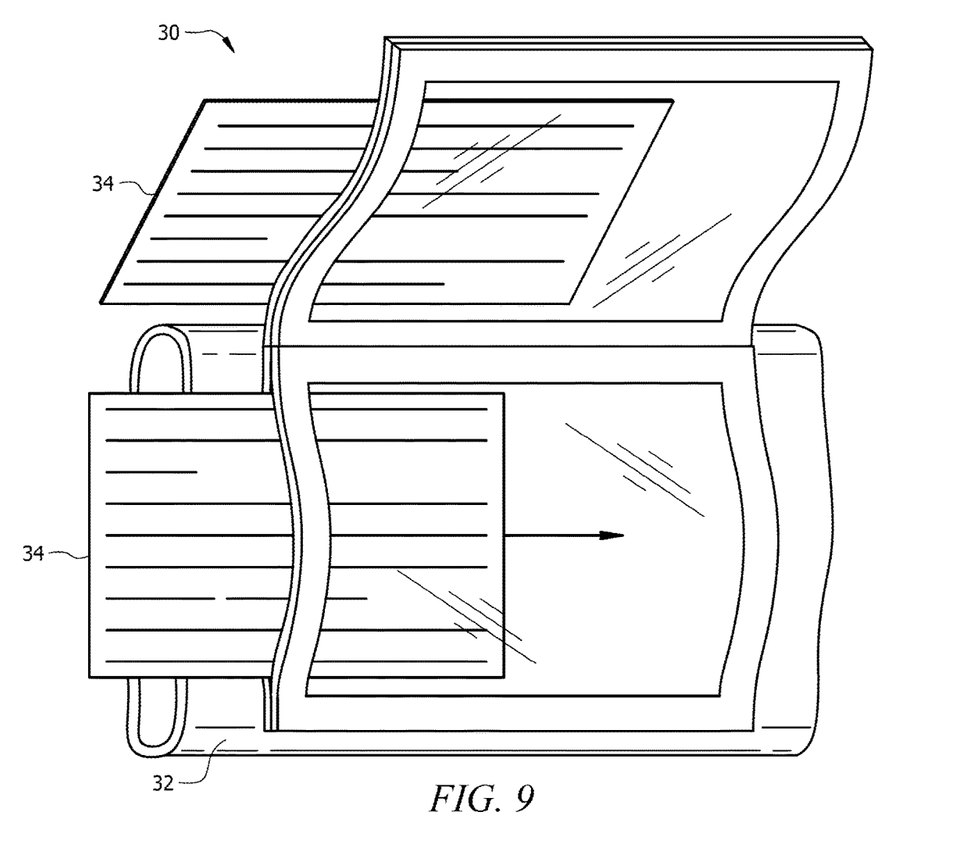
FIG. 9 is a perspective view of the transparent sleeves of the instruction portion of the device illustrating that patient information/medical instructions may be placed within the sleeves.

In the embodiment shown in FIGS. 7-9 in which fastener 32 is in the form of a tubular band, medical information/instruction display 34 may be in the form of printed information/instructions inserted into one or more transparent sleeves 36. Two or more transparent sleeves 36 may be attached to the front side of the tubular band. In this embodiment, each transparent sleeve 36 may be attached to the tubular band longitudinally along at least one edge. The transparent sleeves 36 may be attached so that they are stacked on top of each other as depicted in FIGS. 7 and 8. The edge of transparent sleeve 36 that is not attached to the tubular band may have removable closure device 70 to removably attach that edge to a transparent sleeve 36 that is located beneath it in the stack as illustrated in FIGS. 7 and 8. This allows each transparent sleeve 36 to be folded back from the others and the medical information/instructions to be shown on both the front and back surfaces of each transparent sleeve 36. Attachment of medical information/instruction display 34 would be similar in other embodiments in which at least one strap is used as fastener 32 and medical information/instruction display 34 are printed sheets.

As illustrated in FIG. 8, each transparent sleeve 36 may have an opening on at least one end into which medical information/instruction display 34 as printed medical information/instructions may be inserted. Two sets of medical information/instructions may be contained within each transparent sleeve 36 to allow one set of information/instructions to be viewed on the front surface of transparent sleeve 36 and another set of information/instructions to be viewed on the back surface of transparent sleeve 36.

FIG. 9 depicts an enlarged image of instruction portion 30 of device 10 in which fastener 32 is in the form of at least one strap that is a tubular band capable of encircling a user's arm/wrist, the child's limb or an inanimate object close to the child. As illustrated in FIG. 9, medical information/instruction display 34 are shown as printed cards/paper that may be inserted into transparent sleeves 36. As in FIG. 8, two sets of medical information/instructions may be contained within each transparent sleeve 36 to allow one set of information/instructions to be viewed on the front surface of transparent sleeve 36 and another set of information/instructions to be viewed on the back surface of the transparent sleeve 36.

Figure 10:
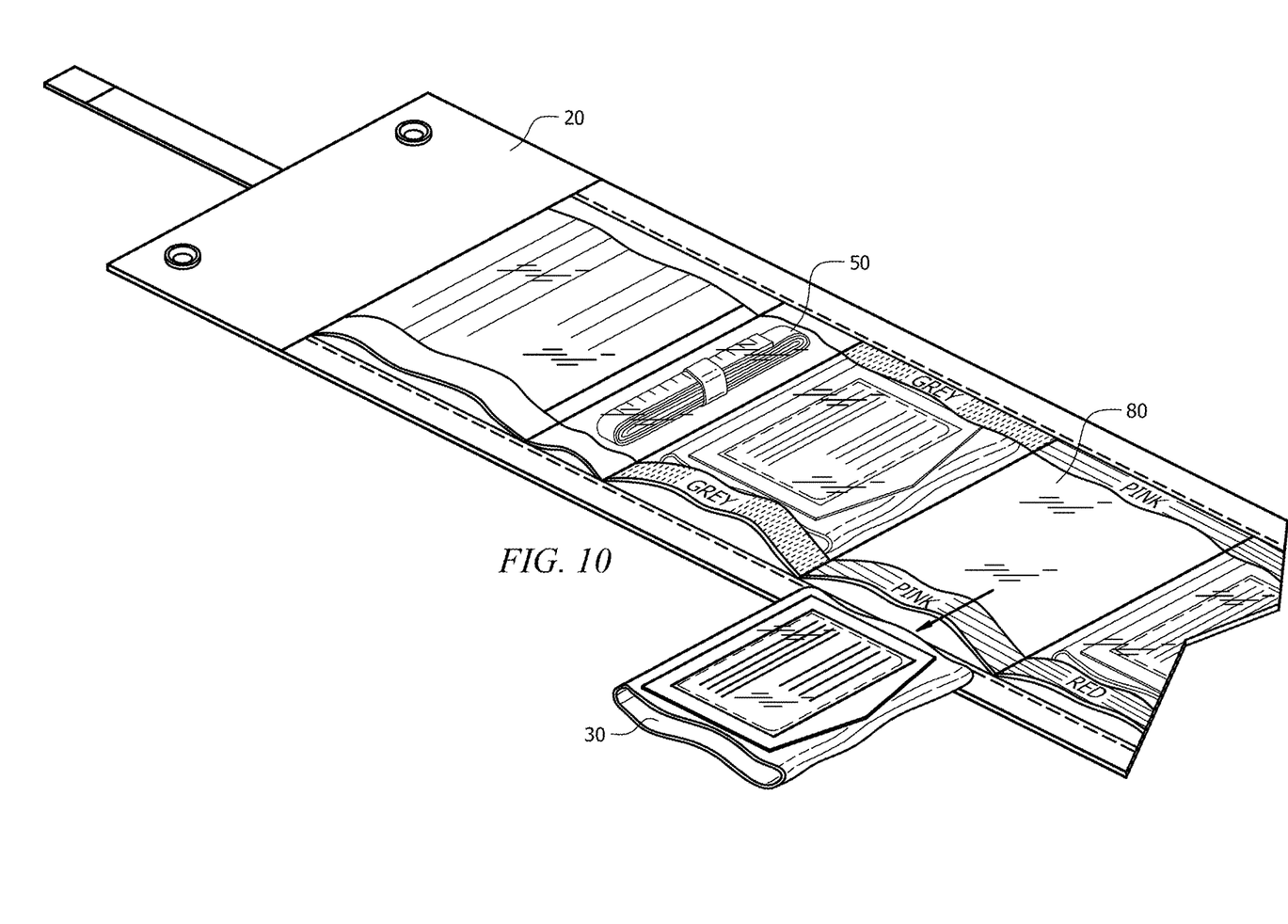
FIG. 10 is a perspective view of an embodiment of the device in which containment devices are used as retaining device. In this specific embodiment, transparent sleeves/pouches are used as the containment devices.
Figure 11:
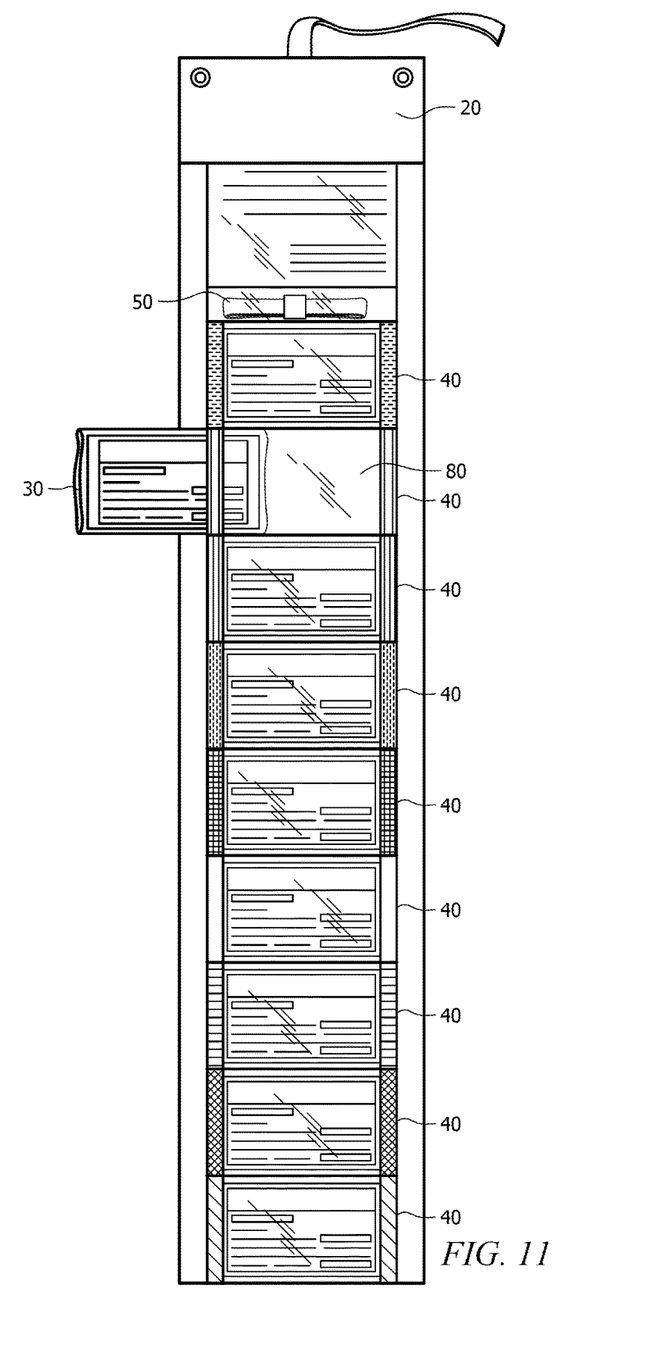
FIG. 11 is a front view of the embodiment of the device in which containment devices are used as the retaining device.

FIGS. 10 and 11 demonstrate an alternative embodiment in which, instead of retaining device 60 being positioned on instruction portion 30 and on elongated base 20, a plurality of containment devices 80 are used as retaining device 60 and are positioned lengthwise along elongated base 20. Each containment devices 80 is capable of holding one color-coded instruction portion 30. Containment devices 80 may be transparent so that instruction portion 30 is visible through containment devices 80. Alternatively, all or a portion of containment devices 80 may be opaque or color-coded to correspond to the color zones 40 on elongated base 20. Containment devices 80 may include, but is not limited to, a pouch, sleeve, pocket, strap, clip, cradle structure having a top and a bottom portion which allows the instruction portion to be contained between the top and bottom portions, etc. One of skill in the art would recognize types of containment devices that may be used in the device.

In an embodiment in which transparent containment devices 80 are used, a section or the edges of each containment devices 80 may be color-coded to correspond to instruction portion 30 contained therein. The color-coded section/edges of containment devices 80 may determine color-coded zones 40 of elongated base 20 in the event base 20 is not color-coded itself.

In use, the child's length/height or weight is first determined. The child may be measured using a resuscitation tape, such as the Broselow® tape or Pediatape, to determine which color zone the child falls into. Alternatively, the child may be weighed to determine which color zone the child falls into. Once the color zone of the child is determined, the medical professional or user would remove instruction portion 30 of device 10 corresponding to color zone 40 of the child from elongated base 20. Instruction portion 30 would then be positioned, using fastener 32, either on the arm or clothing of the medical professional or user, on a limb or clothing of the child or other person adjacent to the child, or alternatively may be attached to an inanimate object near the child, such as the railing of the bed, or to any other surface or inanimate object as long as the medical information can be readily accessible to the medical professional/user while caring for the child.

In addition to the above embodiments, it is contemplated that the device may be used in other medical situations for other patients. For example, the device may be used in a hospital setting or nursing home setting to have valuable patient information, such as allergies and current medications and dosages, easily accessible to someone caring for the patient. Different colors could be assigned to different types of information. For example, current medications could be in a blue color zone while allergies are in a red color zone. The basic structure of the device would remain the same which would allow for the instruction portions of the device to be removed from the base and positioned adjacent to or on the patient or other person near the patient.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween. Now that the invention has been described,

What is claimed is:

1. A medical treatment device for pediatric patients comprising:
    an elongated base; and
    a plurality of removable color-coded instruction portions positioned on the elongated base comprising
        a fastener; and
        a medical information/instruction display attached to the fastener;
    wherein the elongated base is divided into color-coded zones corresponding to a child's weight;
    wherein each of the color-coded zones contains one corresponding color-coded instruction portion containing medical information/instructions for that specific color zone.

2. The device of claim 1, wherein the plurality of removable color-coded instruction portions are positioned on the elongated base by retaining device.

3. The device of claim 2, wherein the retaining device are a plurality of containment devices.

4. The device of claim 1, wherein the fastener is at least one strap.

5. The device of claim 4, wherein the at least one strap is a tubular band.

6. The device of claim 5, wherein the tubular band is elasticized.

7. The device of claim 1, further comprising a resuscitation tape removably retained on the elongated base.

8. The device of claim 1, wherein the medical information/instruction display is at least one sheet having printed medical information/instructions.

9. The device of claim 8, wherein the at least one sheet is encased within at least one transparent sleeve.

10. The device of claim 1, wherein the color-coded zones correspond to color-coded zones on a resuscitation tape.

11. A method of displaying medical instructions comprising:
   determining a child's color zone on a resuscitation tape having color-coded zones based on size of the child;
   correlating the child's color zone to color-coded zones on a device comprising:
      an elongated base having color-coded zones corresponding to the color-coded zones on the resuscitation tape; and
      a plurality of removable instruction portions positioned on the elongated base comprising:
         a fastener; and
         a medical information/instruction display attached to the fastener;
         wherein the instruction portion displays the medical information/instruction display to a user to effectively administer medical care to the child;
         wherein each color-coded zone of the device contains one corresponding color-coded instruction portion containing the medical information/instructions for that specific color zone;
   removing the instruction portion correlated to the child's color zone from the elongated base; and
   removably attaching the instruction portion to an object using the fastener so that the medical information/instruction display may be clearly viewed by the user.

12. The method of claim 11, wherein the child's color zone is determined by measuring the child using the resuscitation tape having color-coded zones based on the child's weight.

13. The method of claim 11, wherein the child's color zone is determined by weighing the child.

14. The method of claim 11, wherein the object to which the instruction portion is removably attached is the user's arm.

15. The method of claim 14, wherein the object to which the instruction portion is removably attached is the child's limb.

16. A system for displaying medical information/instructions comprising:
   an elongated base divided into color coded zones corresponding to a child's weight;
   a plurality of instruction portions positioned on the elongated base comprising
      fastener; and
      a medical information/instruction display attached to the fastener;
      wherein the instruction portion displays the medical information/instruction display to a user to effectively administer medical care to the child;
   wherein each color-coded zone contains one corresponding color-coded instruction portion containing the medical information/instructions for that specific color zone;
   wherein a child's weight is determined and the child's weight is correlated to a specific color zone on the elongated base;
   wherein the instruction portion correlated to the child's color zone is removed from the elongated base; and
   wherein removably attaching the instruction portion to an object allows the medical information/instruction display to be clearly viewed by the user.

17. The system of claim 16, wherein the child's weight is determined by the child being measured using a resuscitation tape having color-coded zones based on the child's weight.

18. The system of claim 17, wherein the color-coded zones on the resuscitation tape are correlated to the color-coded zones on the elongated base.

19. The system of claim 16, wherein the medical information/instruction display is at least one sheet having written medical information/instructions.

20. The method of claim 16, wherein the object to which the instruction portion is attached is selected from the group consisting of the user's arm, the child's limb, a person's arm adjacent the child, and an inanimate object adjacent the child.

* * * * *